US012746337B2

(12) United States Patent
Canesi

(10) Patent No.: US 12,746,337 B2
(45) Date of Patent: Sep. 29, 2026

(54) SYRINGE PLUNGER BRACE FOR IMPROVED ASPIRATION AND INJECTION

(71) Applicant: Jennifer Canesi, Boston, MA (US)

(72) Inventor: Jennifer Canesi, Boston, MA (US)

( * ) Notice: Subject to any disclaimer, the term of this patent is extended or adjusted under 35 U.S.C. 154(b) by 1113 days.

(21) Appl. No.: 17/850,199

(22) Filed: Jun. 27, 2022

(65) Prior Publication Data

US 2023/0181834 A1 Jun. 15, 2023

Related U.S. Application Data

(63) Continuation-in-part of application No. 17/550,779, filed on Dec. 14, 2021, now abandoned.

(51) Int. Cl.
*A61M 5/31* (2006.01)
*A61M 5/32* (2006.01)

(52) U.S. Cl.
CPC ............ *A61M 5/3148* (2013.01); *A61M 5/32* (2013.01); *A61M 2202/0007* (2013.01)

(58) Field of Classification Search
CPC ................ A61M 5/3148; A61M 5/317; A61M 2005/3139; A61M 2205/586; A61M 5/3135
See application file for complete search history.

(56) References Cited

U.S. PATENT DOCUMENTS

| | | | | |
|---|---|---|---|---|
| 2,823,675 | A | 2/1958 | Sciurba | |
| 2,842,128 | A | 7/1958 | Hein, Jr. | |
| 4,217,896 | A | 8/1980 | Behnke | |
| 4,324,241 | A | 4/1982 | Reese | |
| 4,351,334 | A * | 9/1982 | Inglefield, Jr. ...... | A61M 5/3148 604/227 |
| 4,465,478 | A | 8/1984 | Sabelman | |
| 4,687,472 | A | 8/1987 | Gross | |
| 4,767,413 | A | 8/1988 | Haber | |
| 5,833,668 | A | 11/1998 | Aguilar | |
| 6,719,735 | B1 | 4/2004 | Gammon | |
| 10,842,940 | B1 | 11/2020 | Pusateri | |
| 10,973,982 | B2 | 4/2021 | Keating | |
| 2004/0073172 | A1 | 4/2004 | Acha Gandarias | |
| 2012/0220948 | A1 * | 8/2012 | Barbour .............. | A61M 5/3137 604/218 |
| 2014/0163479 | A1 | 6/2014 | Orr | |
| 2017/0290987 | A1 | 10/2017 | Mandaroux | |
| 2023/0062767 | A1 * | 3/2023 | Sciore ................. | A61M 5/3148 |

FOREIGN PATENT DOCUMENTS

| | | | |
|---|---|---|---|
| GB | 2 196 533 | A | 5/1988 |
| WO | 2016070265 | A1 | 5/2016 |

* cited by examiner

*Primary Examiner* — James D Ponton
*Assistant Examiner* — Hong-Van N Trinh
(74) *Attorney, Agent, or Firm* — Lambert Shortell & Connaughton; David J. Connaughton, Jr.; Justin P. Tinger

(57) ABSTRACT

A syringe plunger loop for improved aspiration and injection is disclosed herein. Generally, the loop disclosed herein improves both aspiration and injection by providing stability to the aspiration or injection finger or thumb of the injector. The loop disclosed herein may be integrally attached to the plunger of the syringe. Alternatively, the loop may be a separate piece from the syringe that may be removably attached to the plunger.

7 Claims, 15 Drawing Sheets

SYRINGE PLUNGER BRACE FOR IMPROVED ASPIRATION AND INJECTION

BACKGROUND

Technical Field

The present disclosure relates generally to an improved syringe for methods of aspiration and injection. More particularly the present disclosure relates to a syringe plunger brace for improved aspiration and injection.

Description of Related Art

Injection of liquids containing quantities of drugs, hormones, dyes, etc. through the use of syringes is a common practice. Some chemicals can be injected into an individual's vascular system with minimal risk to the injectee. However, some chemicals carry severe risks if they are intravascularly injected. One example of liquid chemicals that carry such risks are dermal fillers. Intravascular injection of dermal fillers carries the risk of infection, deformity, blindness, and even death.

Aspiration of the liquids within the syringe can help determine if the syringe needle was inadvertently injected into a blood vessel. For example, if the barrel of the syringe contains a quantity of blood after aspiration, then the syringe may have been inadvertently injected into a blood vessel. However, even if the syringe does not contain blood after aspiration, minor movements in the position of the needle during aspiration or injection can cause fluids within the syringe to be injected intravascularly.

Therefore, what is needed is a syringe plunger brace for improved aspiration and injection having the following characteristics and benefits over the prior art.

SUMMARY

The subject matter of this application may involve, in some cases, interrelated products, alternative solutions to a particular problem, and/or a plurality of different uses of a single system or article.

In one aspect, a syringe is disclosed. The syringe comprises a needle, a barrel, a barrel flange, and a plunger. The needle is attached to the bottom of the barrel and the barrel flange is attached to the top of the barrel. The barrel defines a cavity where the plunger is inserted. In this aspect, the syringe also comprises a loop or brace attached to the top of the plunger.

In another aspect, a plunger loop is disclosed. In this aspect, the plunger loop comprises a loop portion and a clip portion, and the loop portion is connected to the clip portion. The clip portion defines an aperture which engages with the plunger of the syringe when the plunger loop is attached to the syringe.

In yet another aspect, a method of using a syringe containing a quantity of liquid is disclosed. The syringe comprises a loop attached to the plunger of the syringe, and the method comprises the following steps: grasping the barrel; inserting the needle into a dermal surface; aspirating by pulling back on the loop attached to the syringe; and injecting after aspirating by pushing down on the loop attached to the syringe, only when the quantity of liquid in the syringe does not contain blood.

It should be expressly understood that the various physical elements of the present disclosure summarized and further disclosed herein may be of varying sizes, shapes, or otherwise dimensions and made from a variety of different materials or methods of manufacture without straying from the scope of the present disclosure.

DETAILED DESCRIPTION

Figure 1:
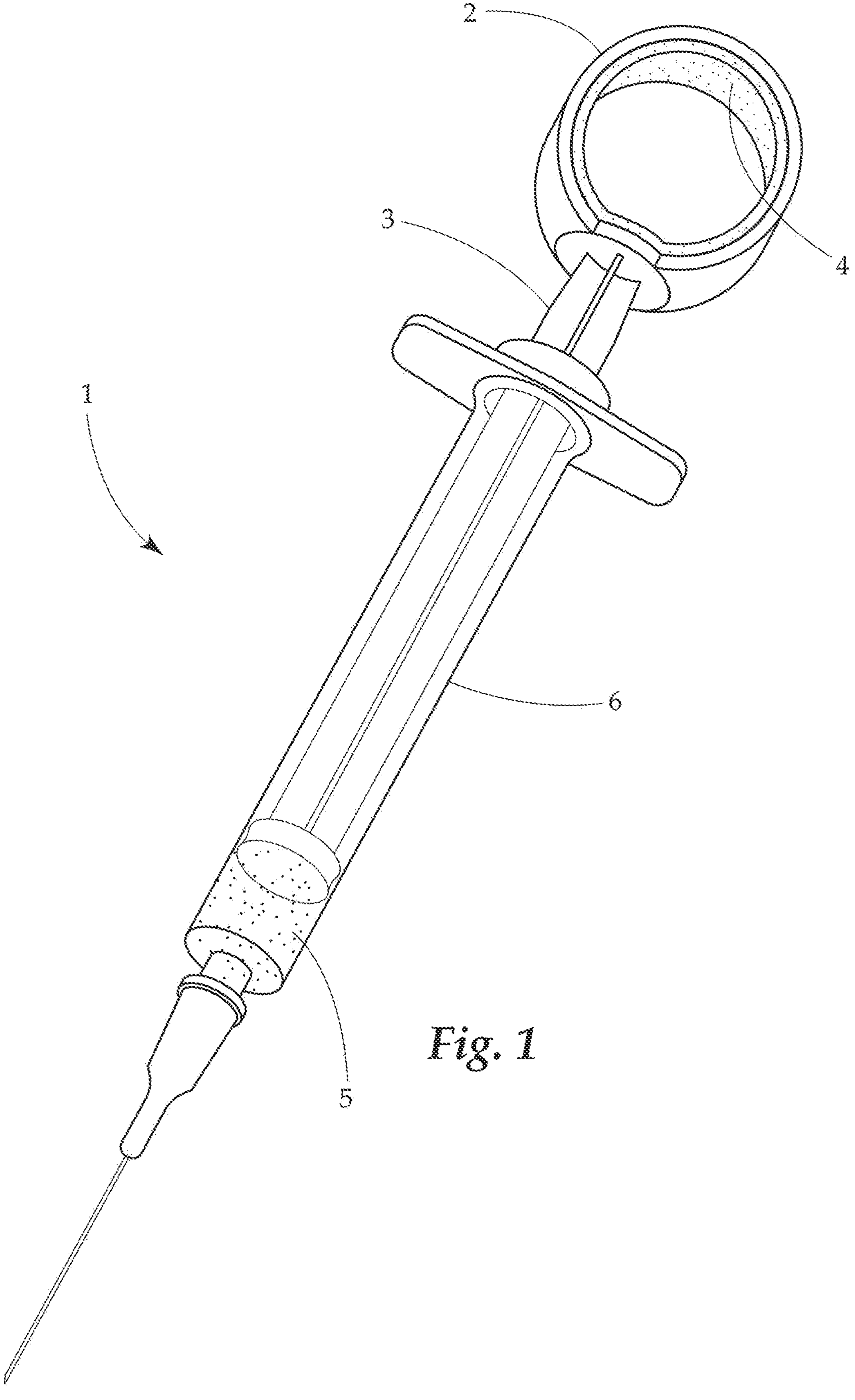
FIG. 1 provides a perspective view of an embodiment of the present disclosure.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a syringe and a plunger loop for improved aspiration and injection. When the syringe and plunger loop are combined, improved products and methods are provided. The terms "loop" and "brace" may be used interchangeably throughout this description. Improving syringe products as well as methods of aspiration and injection is particularly important in the field of cosmetic skin fillers because many dermal fillers can cause complications when injected directly into the blood stream. These complications include, but are not limited to, infection, swelling, blindness, necrosis, and even death. The risks of such complications are compounded by the fact that the use of facial cosmetic fillers is widespread and increasing. The face is one of the most exposed vascular areas of the body, which greatly increases the risk of inadvertent intravascular injection of dermal fillers.

The syringe plunger loop disclosed herein may generally improve aspiration and injection by providing stability for the aspirating or injecting finger or thumb of the injector. In some embodiments, the loop is integrally attached to the plunger of the syringe. In other embodiments, the loop is a separate piece that may be removably attached to the plunger.

In most embodiments, the loop may be attached to the top of the plunger. In one embodiment, the loop is substantially circular in shape. In another embodiment, the loop may have a substantially ovular shape. The loop having a substantially circular or a substantially ovular shape means the shape of the loop is closest to that of a circle or an oval, respectively. In yet another embodiment, the loop is partially conical in shape. The loop having a partially conical shape means the circumference of the loop on one side of the loop is greater than the circumference of the loop on another side of the loop. Furthermore, in another embodiment, the loop may have a substantially tubular shape. As with the other shapes described herein that are modified by the term "substantially," this means that the shape of the loop in this particular embodiment may most closely resemble that of a tube. The tubular shaped loop of this one particular embodiment may also be referred to as a "thumb cradle" or a "brace". As with all other embodiments disclosed herein, the preceding list of shapes is non-exhaustive of the potential shapes the loop may have without straying from the scope of the present disclosure.

To provide stability, in one embodiment, at least a portion of the interior of the loop is lined with a soft padding that allows the loop to firmly engage with an injecting thumb or finger of the injector. The soft padding may be any material, but in one embodiment, the padding material is a foam material. In some embodiments, the entirety of the interior of the loop is lined with the soft padding; however, in other embodiments, only portions of the interior of the loop are lined with the soft padding. For example and without limitation, in one embodiment only the top portion of the interior of the loop is lined with the soft padding. The soft padding may be attached to the interior of the loop by many different methods; however, in one embodiment, the soft padding is adhered to the interior of the loop.

In another embodiment, increased stability may also be provided by a cross-bar attached to the loop. In most embodiments, the cross-bar may be attached to the top, interior of the loop. In one embodiment, the cross-bar may be attached to the interior of the loop by a connector that extends away form the loop. However, in another embodiment, the cross-bar may be attached directly to the top of the loop. In some embodiments, the cross-bar may extend away from the loop on both sides of the loop; however, in other embodiments, the cross-bar may extend away from the loop on only one side of the loop. In some embodiments, the cross-bar is a horizontal cross-bar, wherein a portion of the cross-bar extends away from the loop on both sides of the loop. In other embodiments, a portion of the horizontal cross-bar may extend away from only one side of the loop.

The cross-bar being horizontal means that the angle between the longitudinal, central axis of the cross bar and the point on the loop where the cross-bar is connected is approximately 90°. In other embodiments, the cross-bar may be an angled cross-bar. The cross-bar being an angled cross-bar means that the angle between the longitudinal, central axis of the cross bar and the point on the loop where the cross-bar is connected is greater than or less than approximately 90°. Either an angled or a horizontal cross-bar may provide increased stability; however, as described further herein, an angled cross-bar may provide stability for a wider variety of injecting finger or thumb circumferences than a horizontal cross-bar.

In another embodiment, the loop may be a detachable loop. The detachable loop may be separate from the syringe and may be removably attached to the plunger of the syringe. The detachable loop may have a loop portion and a clip portion. In some embodiments, the detachable loop may have a loop portion and a clip portion on the same integrally connected piece. However, in other embodiments, the loop portion and the clip portion may be separate pieces that connect together to form the detachable loop. Depending on the embodiment, the loop portion may embody any number of shapes without straying from the scope of the present disclosure. Some non-exhaustive examples of potential shapes include: a substantially circular shape, a substantially ovular shape, a partially conical shape, and a substantially tubular shape.

Similar to the loop portion, the clip portion may embody any number of shapes without straying from the scope of the present disclosure. For example, in one embodiment the clip portion may comprise an exoskeleton that engages with at least the plunger of the syringe. In the embodiment where the clip portion comprises an exoskeleton, the exoskeleton may comprise a pocket and a slider, wherein the pocket engages with the plunger flange on the top of the plunger and the slider engages with the plunger. The pocket and the slider may engage with the plunger flange and the plunger, respectively, by at least partially encompassing the plunger flange and the plunger. In most embodiments that embody an exoskeleton, the slider may be capable of two-way translational motion, such that the slider may be depressed and aspirated, which, may cause the plunger that the slider is engaged with to also be correspondingly depressed or aspirated. The exoskeleton may also engage with a portion of the barrel and the barrel flange of the syringe by encompassing a portion of the barrel and the barrel flange. However, in some embodiments, the barrel flange may be removed from the syringe, and the exoskeleton may comprise its own integrally formed barrel flange as a substitute barrel flange for the user.

In some embodiments the clip portion of the detachable loop defines an aperture for engaging with the plunger of the syringe. In the embodiment where the clip portion comprises an exoskeleton, the entirety of the exoskeleton that engages with any part of the syringe by encompassing said part or parts may be referred to as an aperture. The aperture may be of varying shapes and sizes depending on the size and type of plunger the detachable loop is to engage with. For example, the size of syringe plungers vary with the volumetric capacity of the syringe barrel. Accordingly, the size of the detachable loop aperture may vary, depending on the embodiment, to accommodate varying sizes of syringe plungers. To take another example, the shape of syringe plungers may vary. Some syringe plungers have grooves. Accordingly, the shape of the detachable loop aperture may vary, depending on the embodiment, to accommodate the varying shapes of syringe plunger. Particularly, in one embodiment, the detachable loop aperture may be the shape of a cross to engage with each of the grooves of a grooved plunger; however, the aperture may form the shape of a circle, a square, etc., depending on the shape of the plunger.

In one embodiment, the detachable loop may also have a clip portion attached to the loop portion, wherein the clip portion comprises a clip defining the aperture. Similar to the aperture, the size and shape of the clip may vary depending on the size and shape of the plunger. When the detachable loop is attached to the plunger, the clip engages with the plunger of the syringe so that the detachable loop may not be slidably removed from the plunger in any direction. In most embodiments of the detachable loop that comprise a clip, the clip may initially engage with the plunger of the syringe by bending or flexing around the plunger when the clip is pressed against the plunger. In some embodiments, after the clip fully engages with the plunger, the clip may snap back into its initial position (i.e., the rest position of the clip when no external force is applied to it). In other embodiments, the clip may have to be manually bent out of and back into its rest position to be completely attached to the plunger.

Whether the clip automatically bends and reverts back to an initial rest position or whether the clip must be manually bent out of and back into its rest position depends on the material the clip is made from. The clip may be made from any material; however, in one embodiment where the clip automatically reverts back to an initial rest position after attachment to the plunger, the clip may be made from a flexible plastic material. In this embodiment, the plastic material may be stiff enough to prevent the loop from being detached by an aspirating force, yet flexible enough to allow a lateral force to cause the bending of the clip. In another embodiment where the clip must be manually bent out of and back into a rest position, the clip may be made from a flexible steel material.

In yet another embodiment, a portion or the entirety of the detachable loop may be made from a flexible material. For example, in this embodiment, the detachable loop may comprise a loop portion and a prong portion, and the loop portion and the prong portion may be made from the same flexible material. In a preferred embodiment, the flexible material may comprise a rubber material; however, other flexible materials may be used, such as silicone. In this embodiment, the detachable loop and the prongs may be integrally connected, such as, by being formed from the same flexible material mold during a manufacturing process. In this embodiment, the flexible detachable loop may be connected to a base of the prongs. The flexible detachable loop may be connected to a plunger flange by urging the flange into the space between the base of the prongs, and the plunger into the space or aperture between the prongs themselves. The flexibility of the material may allow the flexible detachable loop to be attachable to a wide variety of syringe plungers.

Turning now to FIG. 1, which shows a perspective view of an embodiment of the loop 2 attached to the top of a plunger 3 of a syringe 1. In this embodiment, foam 4 is attached to the interior of the loop 2. The foam 4 allows the loop 2 to achieve a tight fit with thumbs or fingers of varying sizes. Furthermore, the barrel 6 of the syringe 1 contains a quantity of dermal filler 5.

Figure 2:
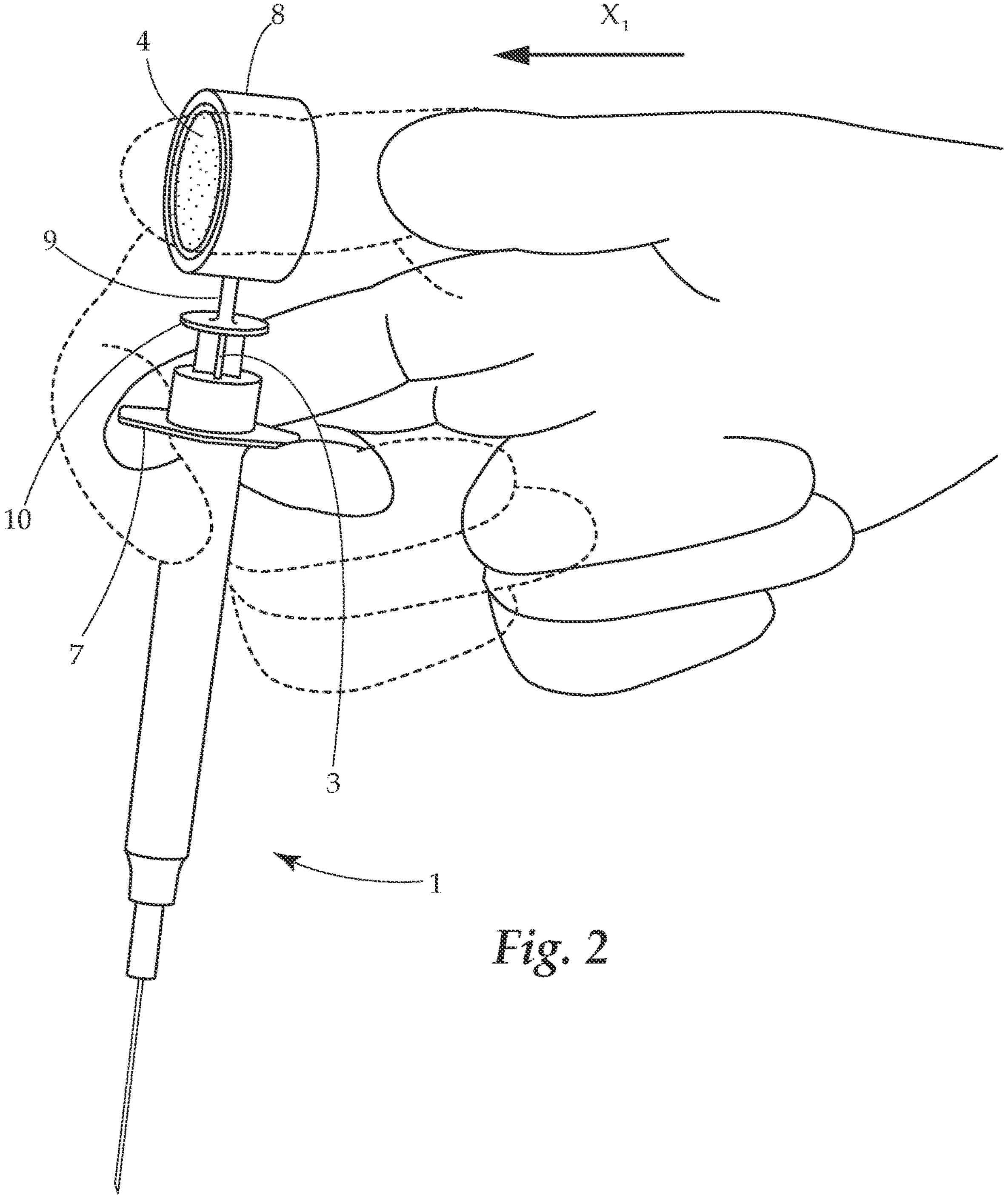
FIG. 2 provides a perspective view of another embodiment of the present disclosure.

FIG. 2 shows another embodiment of an improved syringe 1 comprising a partially conical loop 8 attached to the plunger flange 10 attached to the top of the plunger 3. In this embodiment, the partially conical loop 8 is attached to the plunger flange 10 by a loop connector 9. Moreover, in this embodiment, the loop 8 is partially conical, which means the circumference of the loop 8 on one side of the loop 8 is greater than the circumference of the loop 8 on another side of the loop 8. For example, in this embodiment, as a user's thumb enters the loop 8 in the $X_1$ direction, the loop 8 will feel increasingly tighter to the user as the circumference of the loop 8 decreases in the same direction $X_1$. The decreasing circumference of the partially conical loop 8 further allows for the loop 8 to achieve a tight fit with thumbs or fingers of varying sizes. For example, thumbs that are smaller may need to move further into the partially conical loop 8 to achieve an optimally tight fit. In this embodiment, the tightness of the loop 8 around a user's thumb or finger is also increased by foam 4 being attached to the interior of the loop 8. In this embodiment, the user grips the syringe 1 by grasping the barrel flange 7 and placing their thumb inside the partially conical loop 8.

Figure 3:
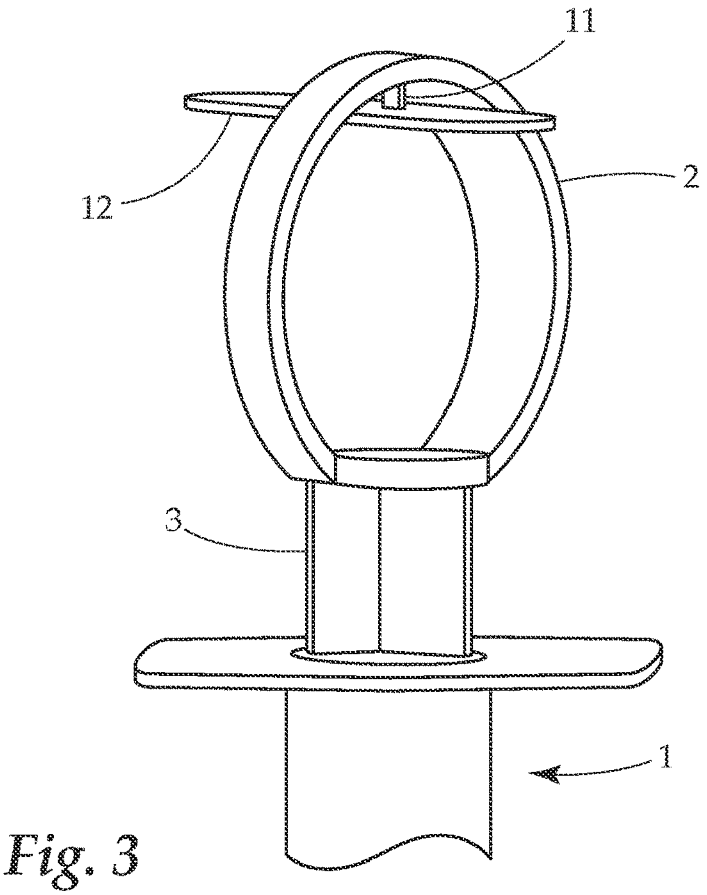
FIG. 3 provides a perspective view of yet another embodiment of the present disclosure.

FIG. 3 shows yet another embodiment of the improved syringe 1 and loop 2 combination. In this embodiment, the loop 2 is attached to the top of the plunger 3, and a cross-bar 12 is attached to the top portion of the interior of the loop 2. In this embodiment, the cross-bar 12 is a horizontal cross-bar 12 which is attached to a cross-bar connector 11, which extends perpendicularly away from the interior of the loop 2. However, in other embodiments, the cross-bar 12 is attached directly to the loop 2.

Figure 4:
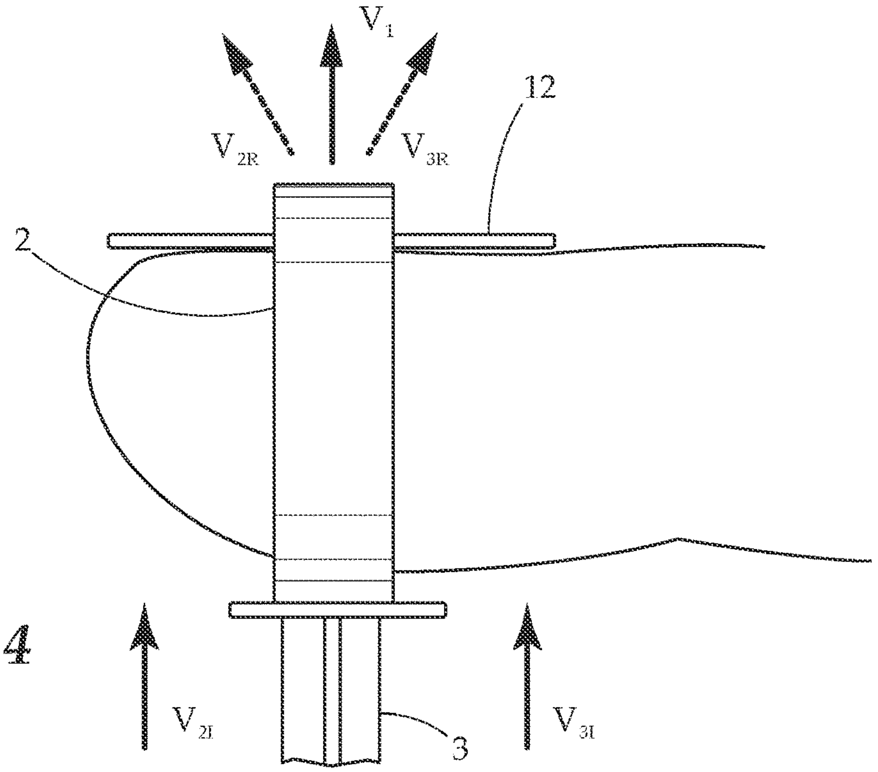
FIG. 4 provides a perspective view of an embodiment of the present disclosure in use.

For example, FIG. 4 shows an embodiment of the loop 2 attached to the top of a plunger 3 wherein the cross-bar 12 is attached directly to the interior of the loop 2. The benefit of the cross-bar 12, similar to the benefit of the partially conical loop 8 and the foam 4 interior for the loop 2 or 8, is that the cross-bar 12 produces a neutral and substantially straight pull vector $V_1$ for the force applied to the plunger 3 during aspiration. Without the cross-bar 12, or similarly the conical shape of the loop 8 and the interior foam 4 in other embodiments, the initial aspirating force vector on one side of the aspirating thumb or finger may become dominant, causing the resulting aspirating pull vector to deviate from a substantially straight path.

For example, and still referring to FIG. 4, without the cross-bar 12, if the initial force vector $V_{2I}$ on the left side of the aspirating thumb or finger becomes too large, this may cause the resulting aspirating pull vector $V_{2R}$ to deviate from a substantially straight path. Similarly, without the cross-bar 12, if the initial force vector $V_{3I}$ on the right side of the aspirating thumb or finger becomes too large, the resulting aspirating pull vector $V_{3R}$ may also deviate from a substantially straight path. Either of these scenarios may cause injection to occur in an unintended area. The horizontal cross-bar 12 prevents either initial force vector $V_{2I}$ or $V_{3I}$ from becoming too large, thus maintaining a neutral aspirating pull vector $V_1$.

Figure 5A:
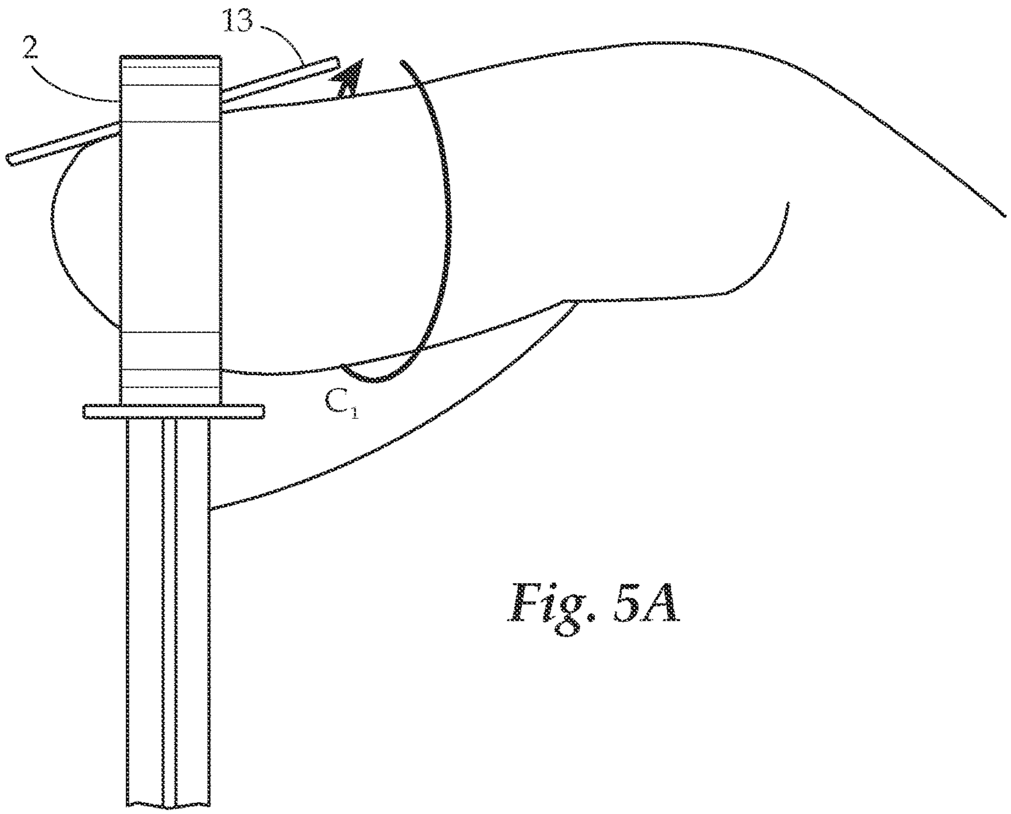
FIG. 5A provides a perspective view of another embodiment of the present disclosure in use.
Figure 5B:
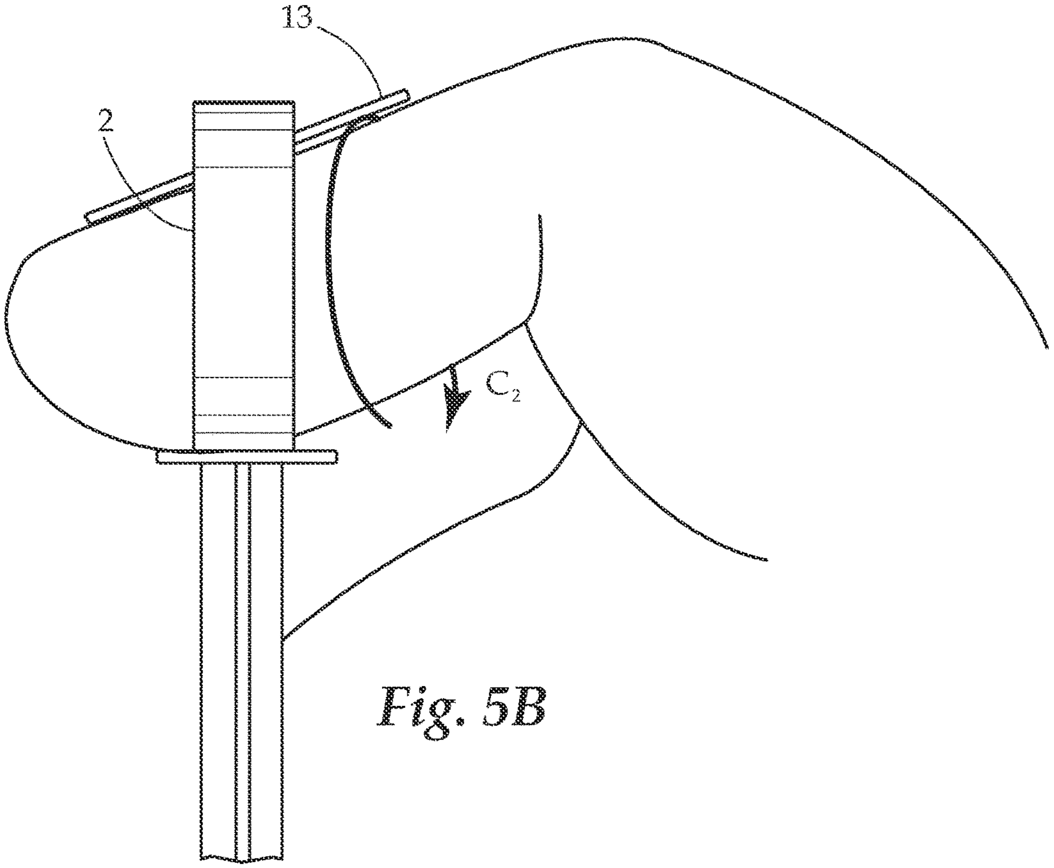
FIG. 5B provides a perspective view of another embodiment of the present disclosure in use.

As can be seen in FIGS. 5A and 5B, an angled cross-bar 13 attached to the inside of the loop 2 also yields a similar benefit to that of other embodiments disclosed herein. The reason for this is that because the cross-bar 13 is angled, thumb or fingers of varying sizes can fit tightly inside the loop 2. For example, in FIG. 5A, the average circumference $C_1$ of the user's thumb or finger is larger than the average circumference $C_2$ of the user's thumb or finger shown in FIG. 5B. Accordingly, the user's thumb or finger in FIG. 5A achieves a tight fit earlier than the user's thumb or finger in FIG. 5B, as can be seen when comparing both figures. In either case, a tight fit can be achieved, regardless of thumb or finger size. The tight fit facilitated by the angled cross-bar 13 has the similar benefit to other embodiments of preventing substantial deviation from a substantially straight path for aspiration and injection because the movement of the aspirating or injection thumb or finger becomes restricted when said thumb or finger is positioned firmly within the loop 2.

Figure 6A:
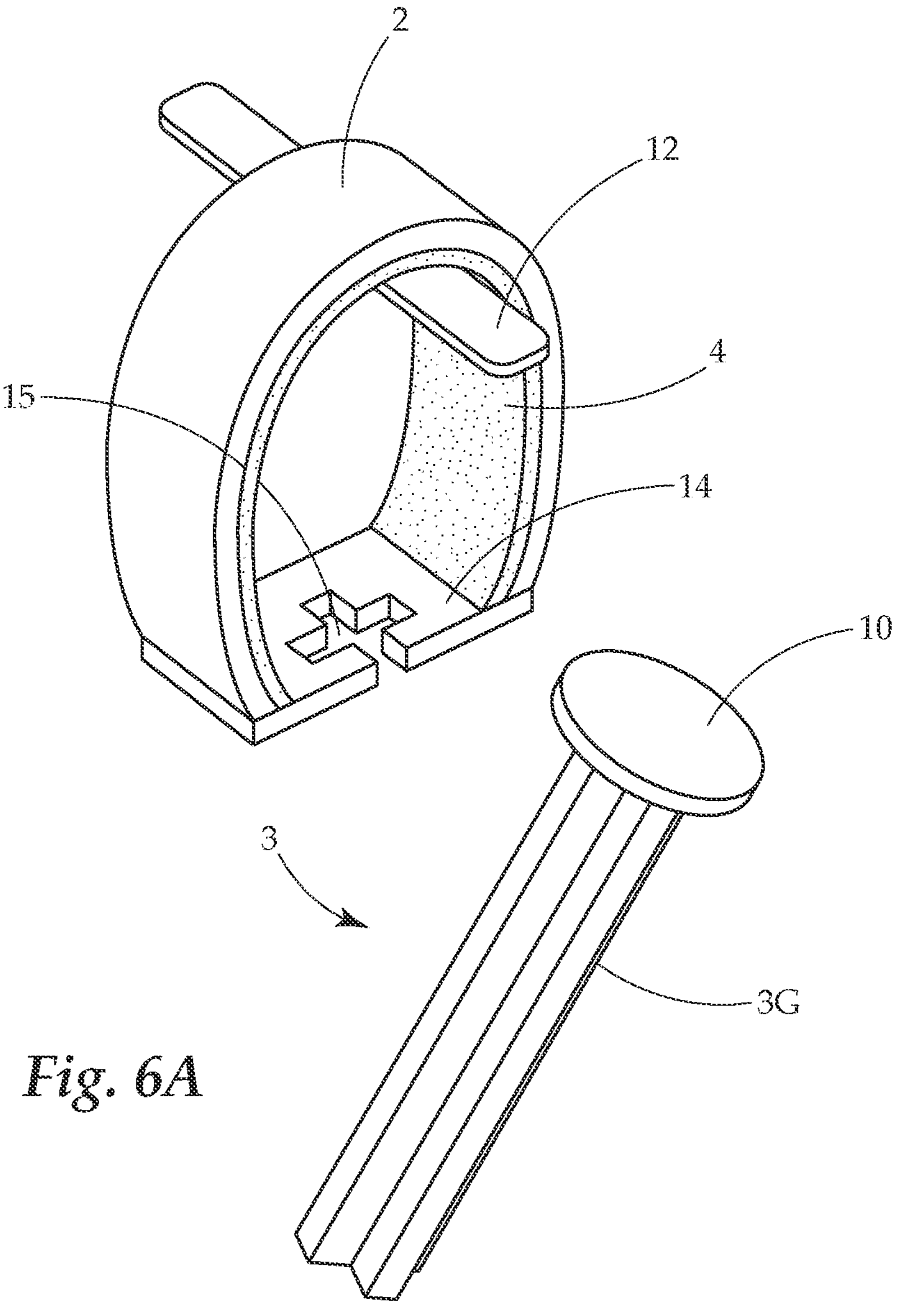
FIG. 6A provides a perspective view of an embodiment of the detachable loop.
Figure 6B:
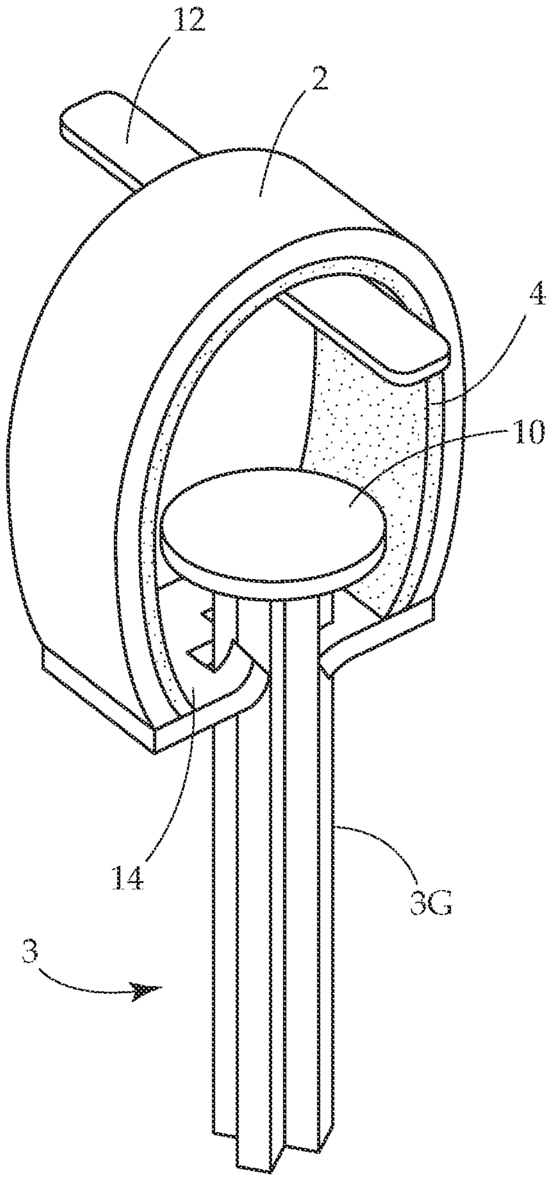
FIG. 6B provides a perspective view of yet another embodiment of the detachable loop interacting with the plunger of a syringe.
Figure 6C:
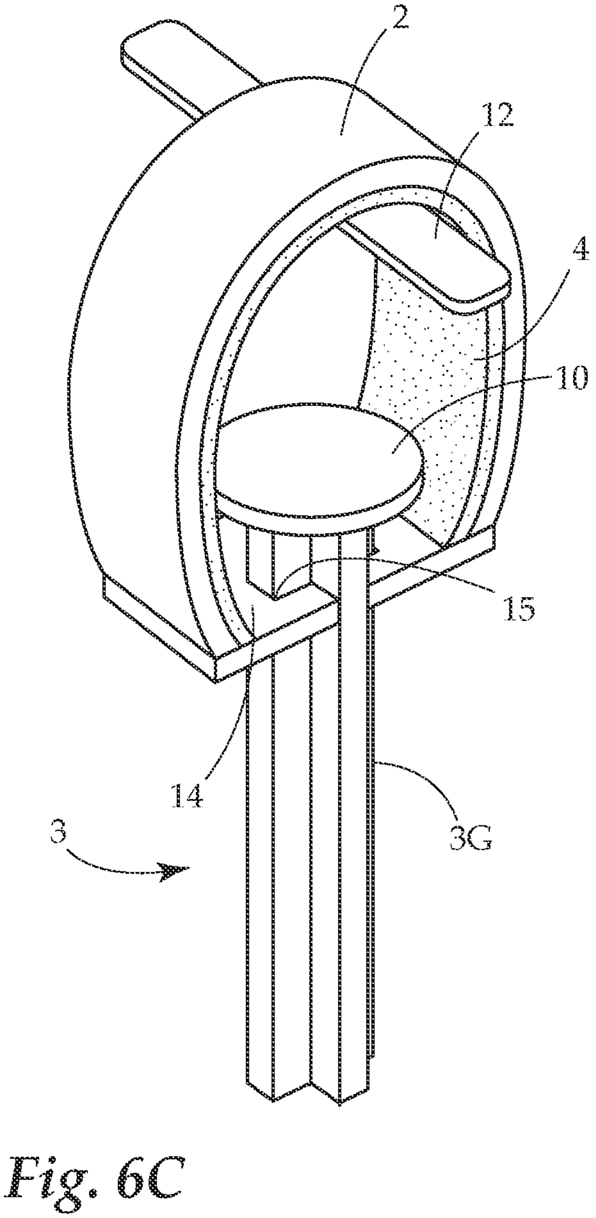
FIG. 6C provides a perspective view of yet another embodiment of the detachable loop engaging with the plunger of a syringe.

FIGS. 6A, 6B, and 6C reveal an embodiment of the present disclosure where the loop 2 is attachable and detachable from the plunger 3 by a clip 14, which, in this embodiment, is attached to the bottom of the loop 2. In this embodiment, a horizontal cross-bar 12 is attached to and extends away from the loop 2 on either side of the loop 2. The loop 2 also comprises foam 4 attached to the interior of the loop 2. In the embodiment shown in FIGS. 6A, 6B, and 6C, the plunger 3 is a grooved plunger 3 that has plunger grooves 3G. In this embodiment, the clip 14 defines an aperture 15 which engages with the plunger grooves 3G when the loop 2 is attached to the plunger 3. In this embodiment, the clip 14 is made from a flexible plastic that bends around the plunger grooves 3G when force is applied to the loop 2 in order to attach the loop 2 to the plunger 3, as can be seen in FIG. 6B. When the loop 2 is fully attached to the plunger 3, the flexible clip 14 bends back to its initial position, as can be seen in FIG. 6C. In this embodiment, the loop 2 is attached to the underside of the plunger flange 10, which is used as a thumb or finger rest when a user's thumb or finger enters the loop 2. When the detachable loop 2 and the plunger 3 are aspirated by a user's thumb or finger, the clip 14 is stiff enough to resist the aspirating force, which prevents the loop 2 from being detached from the plunger 3 by being pulled over the plunger flange 10.

Figure 7:
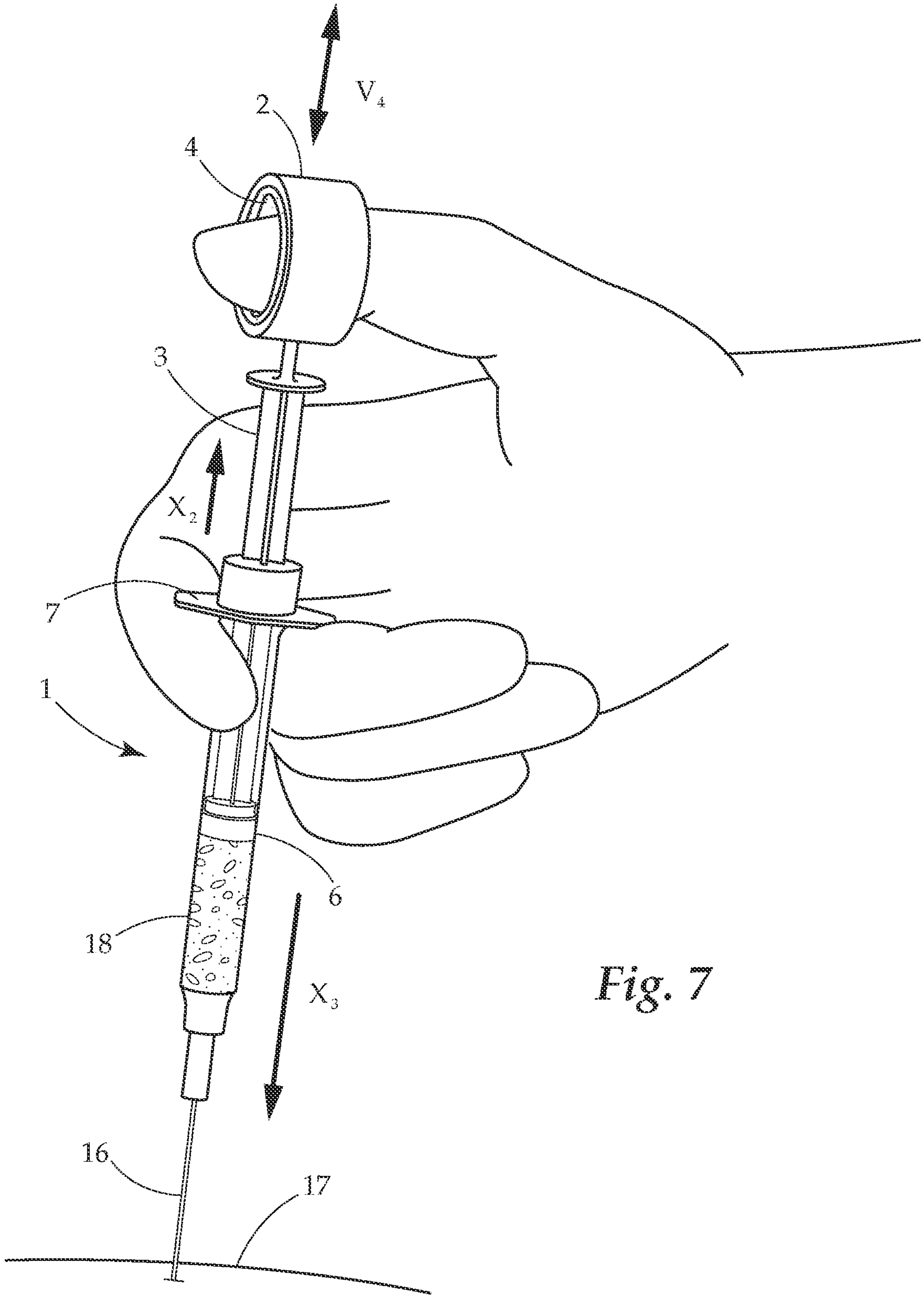
FIG. 7 provides a perspective view of an embodiment of the present disclosure in use on a dermal surface.

FIG. 7 shows an embodiment of the syringe 1 in use. In this embodiment, the loop 2 is attached to and integral with the top of the plunger 3. The loop 2 comprises foam 4 attached or adhered to the interior of the loop 2. In this embodiment, the user grips the syringe 1 by placing their thumb firmly inside the loop 2 and grasping the barrel 6 and wrapping their index and middle fingers around the barrel flange 7. In this embodiment, the foam 4 on the interior of the loop 2 helps the user maintain neutral and substantially straight aspiration and injection force vectors $V_4$. When preparing for injection of a quantity of liquid 18 contained within the barrel 6 of the syringe 1, the injector sticks the needle 16 through a dermal surface 17 of the injectee (e.g., an injectee's skin). Before injecting the quantity of liquid 18 into the injectee, the injector aspirates by pulling back on the plunger 3 in the $X_2$ direction. If the needle 16 penetrated a blood vessel after passing through the dermal surface 17, the quantity of liquid 18 will contain blood after aspiration. If the needle 16 did not penetrate a blood vessel after passing through the dermal surface 17, the quantity of liquid will not contain blood after aspiration. If the liquid 18 does not contain blood, the injector may inject the liquid 18 into the injectee by pushing down on the plunger 3 in the $X_3$ direction.

Figure 8:
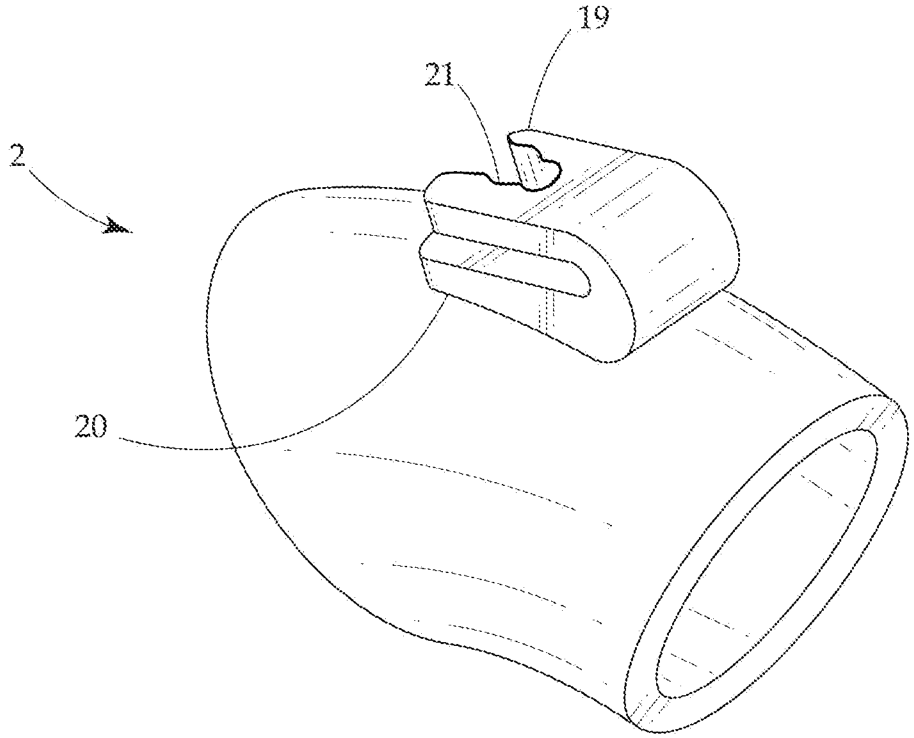
FIG. 8 provides an angled perspective view of another embodiment of a detachable loop.
Figure 9:
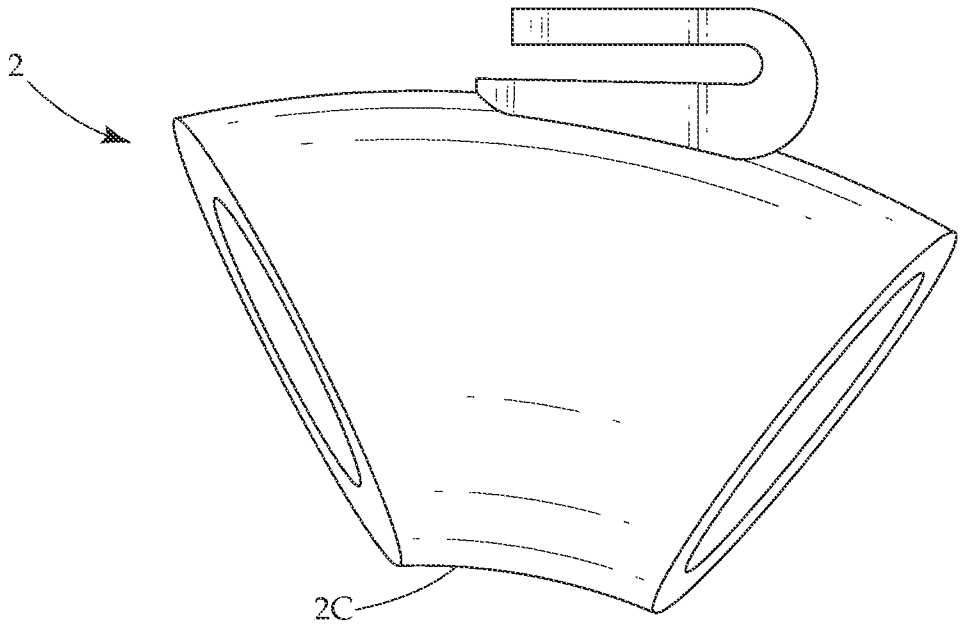
FIG. 9 provides a left side perspective view of an embodiment of a detachable loop.
Figure 10:
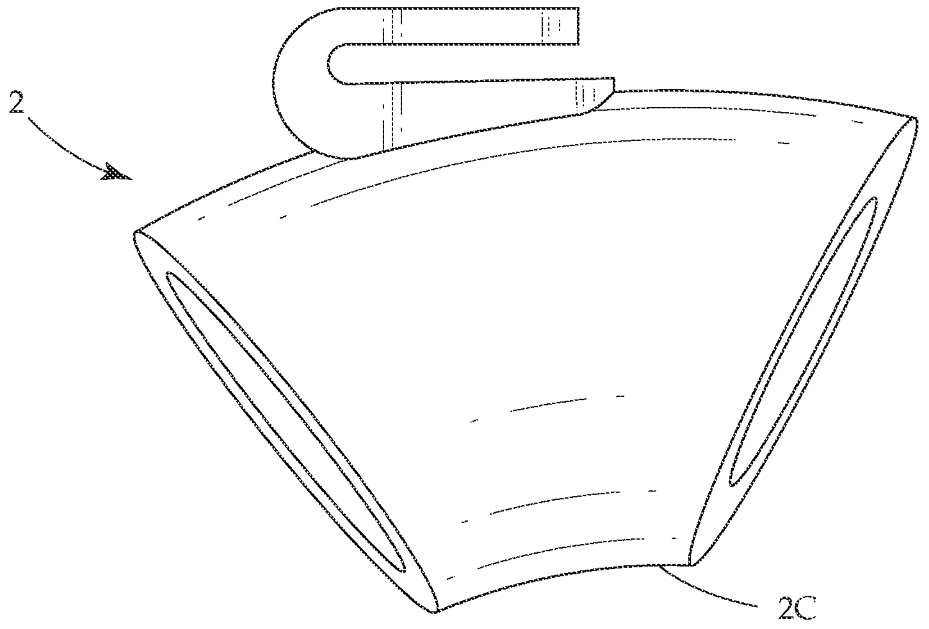
FIG. 10 provides a right side perspective view of an embodiment of a detachable loop.
Figure 11:
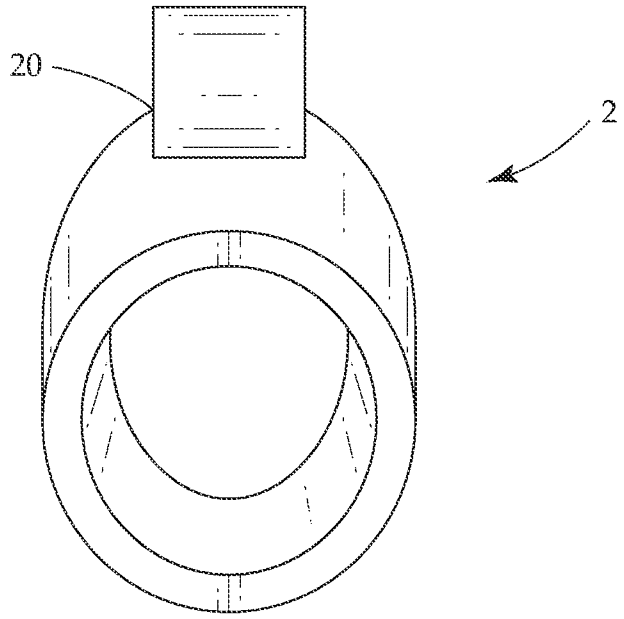
FIG. 11 provides a rear perspective view of an embodiment of a detachable loop.
Figure 12:
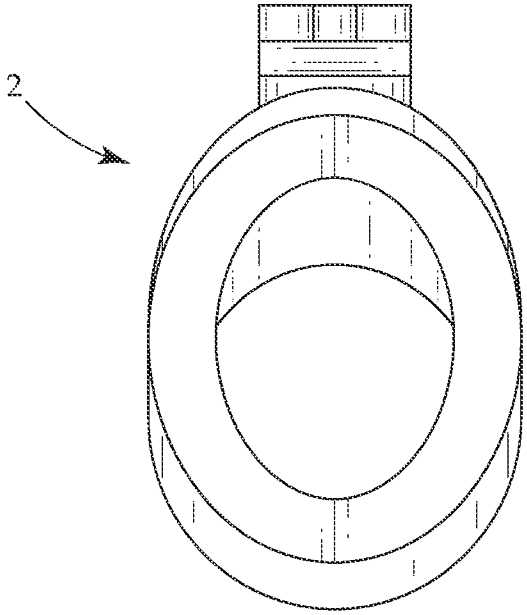
FIG. 12 provides a front perspective view of an embodiment of a detachable loop.
Figure 13:
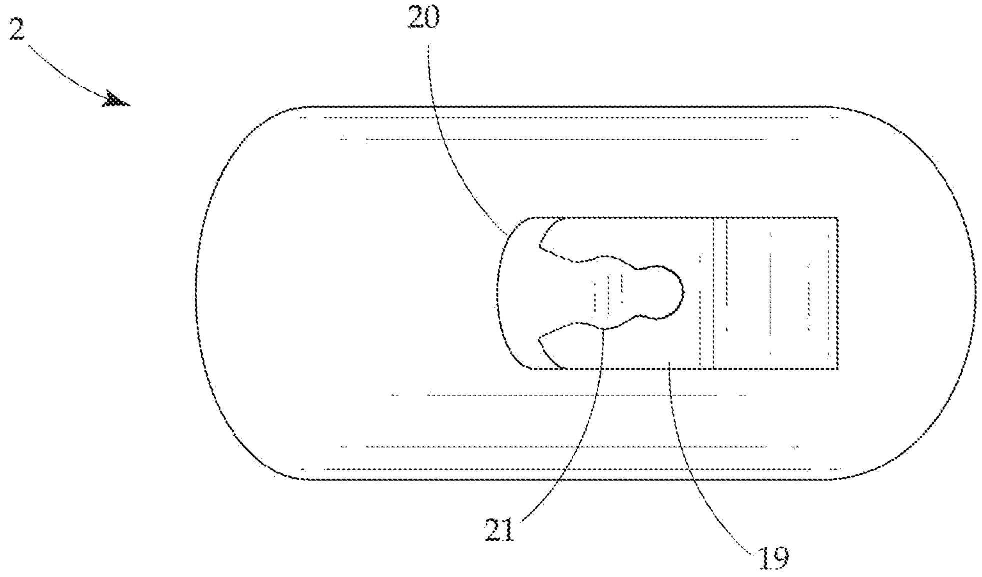
FIG. 13 provides a bottom perspective view of an embodiment of a detachable loop.
Figure 14:
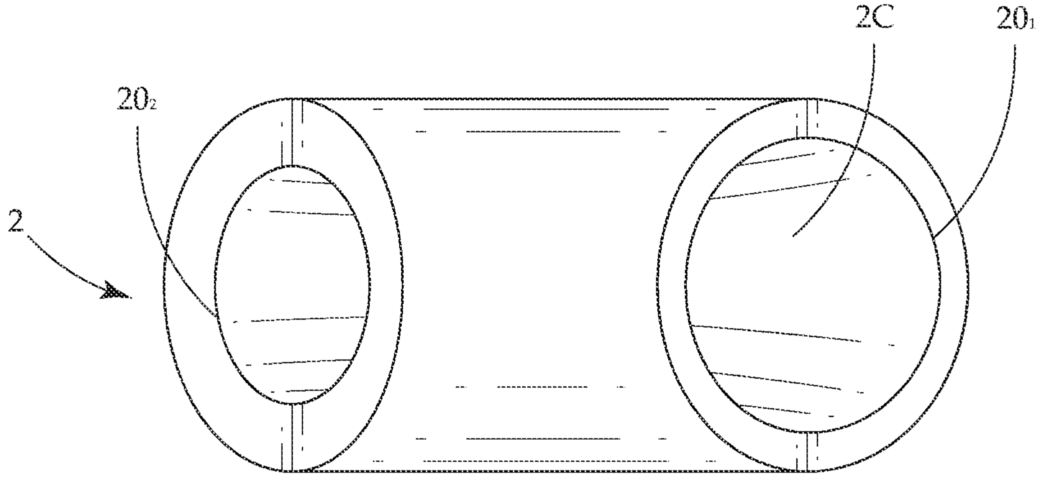
FIG. 14 provides a top perspective view of an embodiment of a detachable loop.

FIGS. 8-15 provide various perspective views of another embodiment of the detachable loop 2 disclosed herein. In this embodiment, the detachable loop 2 comprises a base 20 having two prongs 19. As shown in FIGS. 8 and 13, the detachable loop 2 comprises notched apertures 21 (i.e., multiple different sized apertures) in between the prongs 19. These notched apertures 21 allow the detachable loop 2 to fit on different sized syringe plungers 3. As shown in FIGS. 9, 10, and 14 the interior and exterior circumferences 2C of the loop 2 are curved. This curved circumference 2C provides for a secure fit when a user's thumb or finger is placed in the loop 2. Also, as shown in FIG. 14, the interior diameter $2D_1$, $2D_2$ of the loop tapers inward. In other words, the diameter $2D_1$ at one end of the loop 2 is greater than the diameter $2D_2$ at the other end of the loop 2. This tapered diameter $2D_1$, $2D_2$ causes the loop 2 to tighten around a user's thumb or finger as the user's thumb or finger is pushed farther into the loop 2. This adaptability is critical as this feature allows the loop 2 to comfortably and effectively work with digits of various sizes.

Figure 15:
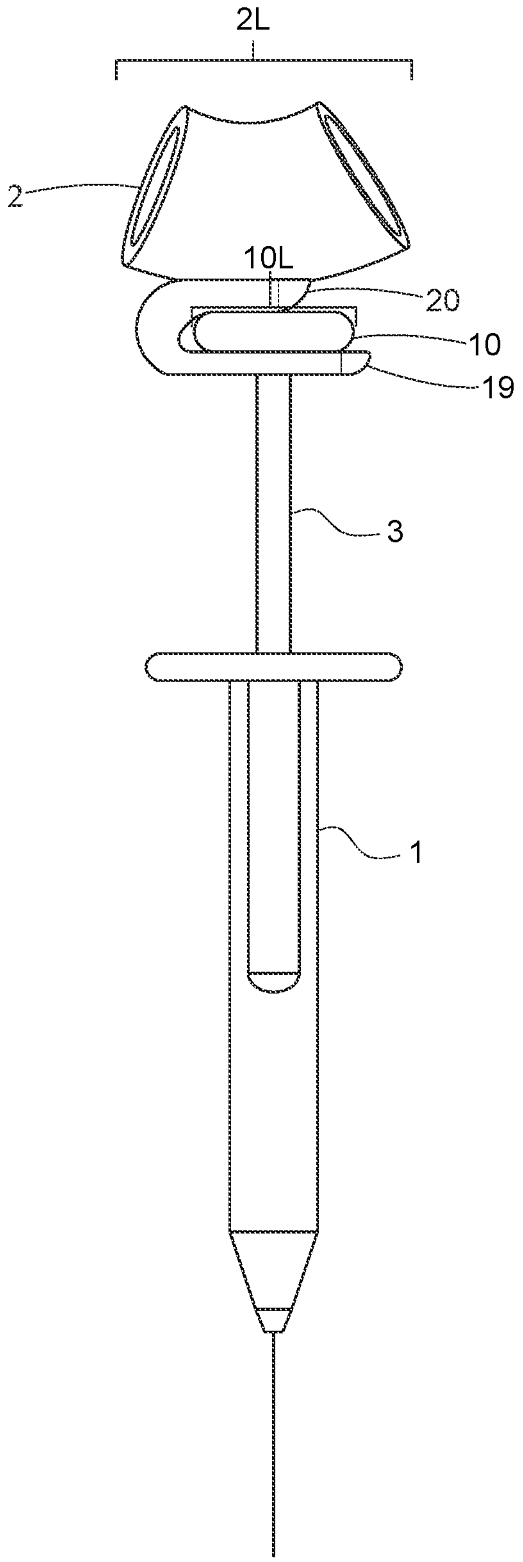
FIG. 15 provides yet another perspective view of an embodiment of the detachable loop engaging with the plunger of a syringe.

Next, as shown in FIG. 15, this embodiment of the detachable loop 2 can be attached to the plunger 3 of a syringe 1 by urging the plunger flange 10 into the space between the base 20 and the prongs 19. In this embodiment, the prongs 19 and the loop 2 are integrally connected at the base 20, and the entirety of the detachable loop 2 comprises a flexible material. In this embodiment, the exact type of material used is critical because the material needs to have a sufficiently high coefficient of friction in order for the detachable loop 2 to stay firmly on the plunger 3 during aspiration and injection. A material has a "sufficiently high" coefficient of friction if it's coefficient of friction is approximately 1 or greater. When used herein, the term "approximately" refers to a range of plus or minus ten percent (10%). Thus, flexible materials such as silicone or rubber are preferable in this embodiment.

Another critical aspect of the embodiment shown in FIGS. 8-15 is that the length the loop 2L is greater than the length of the flange 10L. This allows for a stabilizing connection when the loop 2 is in use, and it also provides a larger surface area for contact with a user's digit, which may provide for greater control of the plunger 3 when the plunger 3 is used in conjunction with the loop 2. Yet another critical aspect of this embodiment is the length differential between the proximal or bottom portion of the loop 2 (i.e., closer to the base 20) and the distal or top portion of the loop 2 (i.e., farther from the base 20). In this embodiment, the distal portion of the loop 2 is shorter than the proximal portion of the loop 2, which allows for a user's thumb to stretch or extend away from the interior of the proximal portion of the loop 2, even when the interphalangeal joint crease of the thumb is facing the proximal portion of the loop 2. This length differential is also critical, not only for aspiration, as described above, but also for injection because the greater size of the proximal portion provides for greater stability when a user's thumb is performing an injection technique in order to expel products from the syringe.

While several variations of the present disclosure have been illustrated by way of example in preferred or particular embodiments, it is apparent that further embodiments could be developed within the spirit and scope of the present disclosure, or the inventive concept thereof. However, it is to be expressly understood that elements described in one embodiment may be incorporated with any other embodiment in combination with any other elements disclosed herein in the various embodiments. It is also to be expressly understood that any modifications and adaptations to the present disclosure are within the spirit and scope of the present disclosure, and are inclusive, but not limited to the following appended claims as set forth.

What is claimed is:

1. A detachable plunger loop comprising:

a loop portion having an interior and an exterior, the interior extending along a length of the loop portion in a lengthwise direction, wherein the loop portion interior comprises a tapered diameter such that a first opening of the interior of the loop portion has a perimeter that is greater than a perimeter of a second opening of the loop portion, the first and second openings being on opposite lengthwise ends of the loop portion;

wherein the interior of the loop portion is tubular in shape and is curved in the lengthwise direction on a proximal portion and a distal portion, wherein a centerline of the curved interior of the loop portion follows an arcuate path such that the first opening faces in a first direction and the second opening faces in a second direction different from the first direction, and wherein the exterior of the loop portion is curved in the lengthwise direction on the proximal portion and the distal portion, such that the exterior of the loop portion defines a curved tubular shape curved in the lengthwise direction;

a prong portion, wherein the loop portion is connected to the prong portion, and the prong portion defines an aperture for engaging with a plunger of a syringe; and wherein the length of the loop portion between the first opening and the second opening is greater than a length of the prong portion.

2. The detachable plunger loop of claim 1 wherein the loop portion comprises a flexible material.

3. The detachable plunger loop of claim 1, wherein the loop portion comprises a circumference, and the circumference consists of a curved surface.

4. The detachable plunger loop of claim 1 wherein the prong portion comprises a flexible material.

5. The detachable plunger loop of claim 1 wherein the loop portion and the prong portion are integrally connected at a base of the prong portion.

6. The detachable plunger loop of claim 1 wherein a proximal portion of the loop portion has a greater length than a distal portion of the loop portion.

7. The detachable plunger loop of claim 1, wherein the prong portion is attached to the plunger of the syringe.

* * * * *